United States Patent
Heinonen et al.

[11] Patent Number: 6,148,816
[45] Date of Patent: Nov. 21, 2000

[54] VENTILATOR FOR INTENSIFIED BREATHING AND VALVE IN PATIENT CONDUIT OF APPARATUS FOR INTENSIFIED BREATHING

[75] Inventors: Erkki Heinonen, Helsinki, Finland; Leif Brömster, Solna, Sweden

[73] Assignee: Instrumentarium Corp., Helsinki, Finland

[21] Appl. No.: 09/109,666

[22] Filed: Jul. 2, 1998

[51] Int. Cl.[7] .................................................. A61M 16/00
[52] U.S. Cl. ............................ 128/205.24; 128/204.18; 128/204.21
[58] Field of Search ......................... 128/204.18, 204.19, 128/204.21, 205.24, 204.23

[56] References Cited

U.S. PATENT DOCUMENTS

| | | | |
|---|---|---|---|
| 3,844,280 | 10/1974 | Smythe | 128/205.13 |
| 4,340,044 | 7/1982 | Levy et al. | 128/204.21 |
| 4,838,257 | 6/1989 | Hatch . | |
| 5,273,031 | 12/1993 | Olsson et al. | 128/204.18 |
| 5,315,989 | 5/1994 | Tobia | 128/205.24 |
| 5,596,984 | 1/1997 | O'Mahony et al. | 128/204.18 |
| 5,791,339 | 8/1998 | Winter | 128/204.19 |
| 5,848,591 | 12/1998 | Weismann | 128/204.22 |
| 5,875,777 | 3/1999 | Eriksson | 128/204.21 |
| 5,954,051 | 9/1999 | Heinonen et al. | 128/205.24 |

FOREIGN PATENT DOCUMENTS 58141  7/1969  Luxembourg .

OTHER PUBLICATIONS

*Single Use Anaesthetic Breathing System Uses Adjustable Pressure Limiting Valve*, Design Engineering, May 1, 1990, pp. 32, 35; XP000128772.

*Primary Examiner*—John G. Weiss
*Attorney, Agent, or Firm*—Andrus, Sceales, Startke & Sawall, LLP

[57] ABSTRACT

The invention relates to a ventilator for intensified breathing, whereby a restrictor valve for an over-pressure in the system, a valve allowing breathing from the atmosphere and a directional valve for inhalation are combined to provide a single safety valve (21) arranged in a gas mixture and inhalation conduit assembly (7, 8), said safety valve being arranged to be controlled by an electric control system (26) of the ventilator. The invention also relates to a valve of the above type.

14 Claims, 2 Drawing Sheets

VENTILATOR FOR INTENSIFIED BREATHING AND VALVE IN PATIENT CONDUIT OF APPARATUS FOR INTENSIFIED BREATHING

BACKGROUND OF THE INVENTION

The invention relates to a ventilator, for intensified breathing and to a valve, arranged in a patient conduit of an apparatus for intensified breathing.

Ventilators are used for intensifying the breathing of patients whose own breathing activity for some reason is inadequate. They are typically applied to patients anaesthetised and relaxated during surgery and to those in intensive care. A conventional ventilator provides a cyclic ventilation of lungs. The main phases of a cycle are inhalation and exhalation. A cycle recurs at a desired, controllable pace. A ventilator at its simplest is primarily in accordance with the preamble of claim 1, the needed pressure being provided e.g. by means of a blower.

Inhalation gas in high power ventilators is most often a mixture of oxygen and nitrogen, whereby an oxygen concentration can be arranged as desired between 21 to 100%. For the controlling of the mixture, ventilators are connected to two pressure tanks. The pressure in the pressure tanks is first brought to a constant level by pressure regulators. The bringing of the pressure to a constant level in the pressure tanks improves, on one hand, the adjustability of flow and reduces, on the other, the requirements set for inhalation valves used for controlling the gas flow in a particular conduit. The gas flows of the conduits are arranged to provide the above mentioned oxygen concentration in the mixture and a desired total flow. The total flow can be either a parameter determined directly by the operator or a desired flow value indirectly calculated by a control system from other parameter settings and/or measurement signals. The control system controls the inhalation valves by comparing a measurement signal proportional to the prevailing gas flow to the desired gas flow and by changing the control settings when needed. In the described system said measurement signal is a flow measuring element, but it can also be a location detector of a closing element of an inhalation valve, a pressure signal, a signal proportional to temperature, or a combination of these.

After the separate gas flows are measured and adjusted, the flows are combined and a gas mixture is produced. At this stage the pressure of the gas mixture measured from an inhalation conduit is in most cases, with sufficient accuracy, the same as it is when delivered to a patient. Said pressure can thus participate also in the determining of said desired gas flow, if the control system has been arranged to adjust a constant pressure delivered to the patient during inhalation. The pressure in the inhalation conduit is measured as a difference pressure in relation to the surrounding air pressure. Other functions included in a module comprise a measurement of the oxygen concentration of the mixture, which can, however, also be located closer to the patient.

From the gas mixture module the gas flow is conveyed along the inhalation conduit to a Y piece, to a second branch of which the patient is connected either through a breathing mask or an intubation tube, a third branch being connected to an exhalation conduit. Inhalation thus takes place by means of an over-pressurised gas mixture delivered from the pressure tank through the inhalation valve to the inhalation conduit, whereby the pressure in the inhalation conduit increases. An exhalation conduit is at the time kept closed by an exhalation valve, so the gas mixture is further conveyed to the lungs, causing also a rise in pressure there.

Exhalation takes place spontaneously when an over-pressure stored in the lungs during inhalation is released. This is achieved by the closing of the inhalation valve(s) and by the opening of the exhalation valve in the exhalation conduit, whereby the pressure of the inhalation and exhalation conduits acting on the patient decreases. The over-pressure in the lungs is thus released as a gas flow through the exhalation conduit. The control system controls the exhalation valves and, when necessary, also the inhalation valves in such a way that the pressure level of an exhalation period is reached as quickly as possible and then kept as constant as possible. For adjusting the pressure of the exhalation period, the ventilator is often provided with a pressure sensor arranged in the exhalation conduit, although in most cases the pressures of the exhalation and the inhalation conduits come very close to each other.

Modern ventilators make full use of the opportunities offered by electronics for controlling a breathing cycle according to settings. The control is performed by arranging the inhalation and exhalation valves to implement parameter settings. These settings include inhalation over-pressure, exhalation over-pressure, inhalation volume and the duration of inhalation and exhalation efforts.

Since a ventilator is a life-supporting apparatus, it must be safe. This requirement for safety means that the apparatus must not cause danger to a patient or to a user during normal operation or in the case of a single malfunction. To ensure this, the ventilator is to be provided with safety circuits, which do not depend on its basic functions and which are activated when a basic function for some reason malfunctions. One of the most critical emergencies a ventilator can cause to a patient is over-pressurisation of the lungs. Over-pressure can damage the lungs in a very short time. Malfunction that can cause an over-pressure can occur e.g. when the exhalation valve is blocked to a closed position or the inhalation valve remains open. In order to prevent damages also in such cases of malfunction a restrictor valve is typically arranged in the ventilators. It is usually located in the gas mixture inhalation conduit.

Prior art comprises two types of functions restricting over-pressure. The more conventional one is a spring-loaded valve. The spring is calibrated to open at a predetermined constant pressure. A typical calibration pressure varies from 10 to 12 kPa. A constant limit pressure does not, however, guarantee a fully sufficient safety circuit, considering the varying needs of patients in intensive care. For patients in critical condition over-pressure can cause danger even before said limit pressures are attained. Another weakness in said safety valve is that it only releases an over-pressure higher than the calibrated pressure limit and in case of a malfunction the patient remains over-pressurised at said pressure limit, instead of the pressure dropping to the level of a normal exhalation pressure.

A more advanced version of this safety valve is to replace the calibrated spring with a control system. This control system keeps the valve closed either electronically or electro-pneumatically. An advantage the control system provides is that it allows the limit pressure to be set according to the patient's needs and, on the other hand, over-pressure to be fully released to the level of the exhalation pressure. The control system for an over-pressure valve comprises a pressure-sensitive element. A signal transmitted by this element is compared with a predetermined limit pressure. When the signal exceeds the limit pressure, the control system opens the restrictor valve of the over-pressure.

Another security feature associated with ventilators used particularly in intensive care is that they allow spontaneous breathing. Although the patients are connected to ventilators, they are often capable of breathing independently and they are allowed to do so. A breathing gas is usually mixed by inhalation valves with a desired oxygen concentration. Should the mixing system become damaged, the prior art solutions open the inhalation conduit to the environment, allowing spontaneous breathing to be continued from the atmosphere. The inhalation conduit is opened using either a separate valve or the function is combined with said overpressure restrictor valve. Irrespective of the method of implementation, it is vital for the normal operation of the ventilator that the valve closes tightly when it is not needed to open, because any leaks would make the gas intended for the patient to flow out, which reduces the patient's breathing volume, causing other critical situations and leak alarms. The probability of leaks naturally grows as the number of opening components in the breathing conduits increases. The apparatus also needs to be cleaned after each patient and the accumulation after cleaning becomes more complex, increasing thus the probability of error.

A supplementary requirement associated with spontaneous breathing is to avoid return breathing, i.e. the mixing of exhalation and inhalation gases. Inhalation and exhalation gases are conveyed to different flow conduits by directional valves arranged in said conduits. In prior art solutions these valves are typically placed in the gas mixture module and in the exhalation valve module. The basic requirement set for these valves is small gas flow resistance to reduce the patient's breathing effort. In the inhalation conduit the directional valve is to be located between the patient and the point of opening of the inhalation conduit. In prior art systems with a combined opening for the inhalation conduit and the over-pressure restrictor valve said directional valve can cause danger when the directional valve prevents gas flow from the patient to the over-pressure restrictor valve, i.e. the function for which said valve is arranged in the apparatus.

BRIEF SUMMARY OF THE INVENTION

An object of the present invention is to eliminate above described shortcomings. This is achieved with a ventilator and a valve of the invention, which are primarily characterized in that a closing element is arranged in a safety valve in such a way that it remains in a closed position by the impact of forces other than gravity, whereby said safety valve also provides a directional valve for inhalation, which closes during exhalation the connection to the atmosphere.

Preferably the valve remains under normal conditions in a closed position primarily from the impact of spring force.

The closing element preferably comprises a part, which is of as small volume but as large surface as possible and e.g. in the form of a plate, cone or ball and which seals against a seat. This kind of closing element structure is advantageous for the closing of the valve when the breathing gas is delivered from a pressure tank and, on the other hand, it makes spontaneous breathing easy when the apparatus is released from an active mode.

BRIEF DESCRIPTION OF THE SEVERAL VIEWS OF THE DRAWING

The invention will be now described in greater detail with reference to the enclosed drawings, in which.

DETAILED DESCRIPTION OF THE INVENTION

Figure 1:
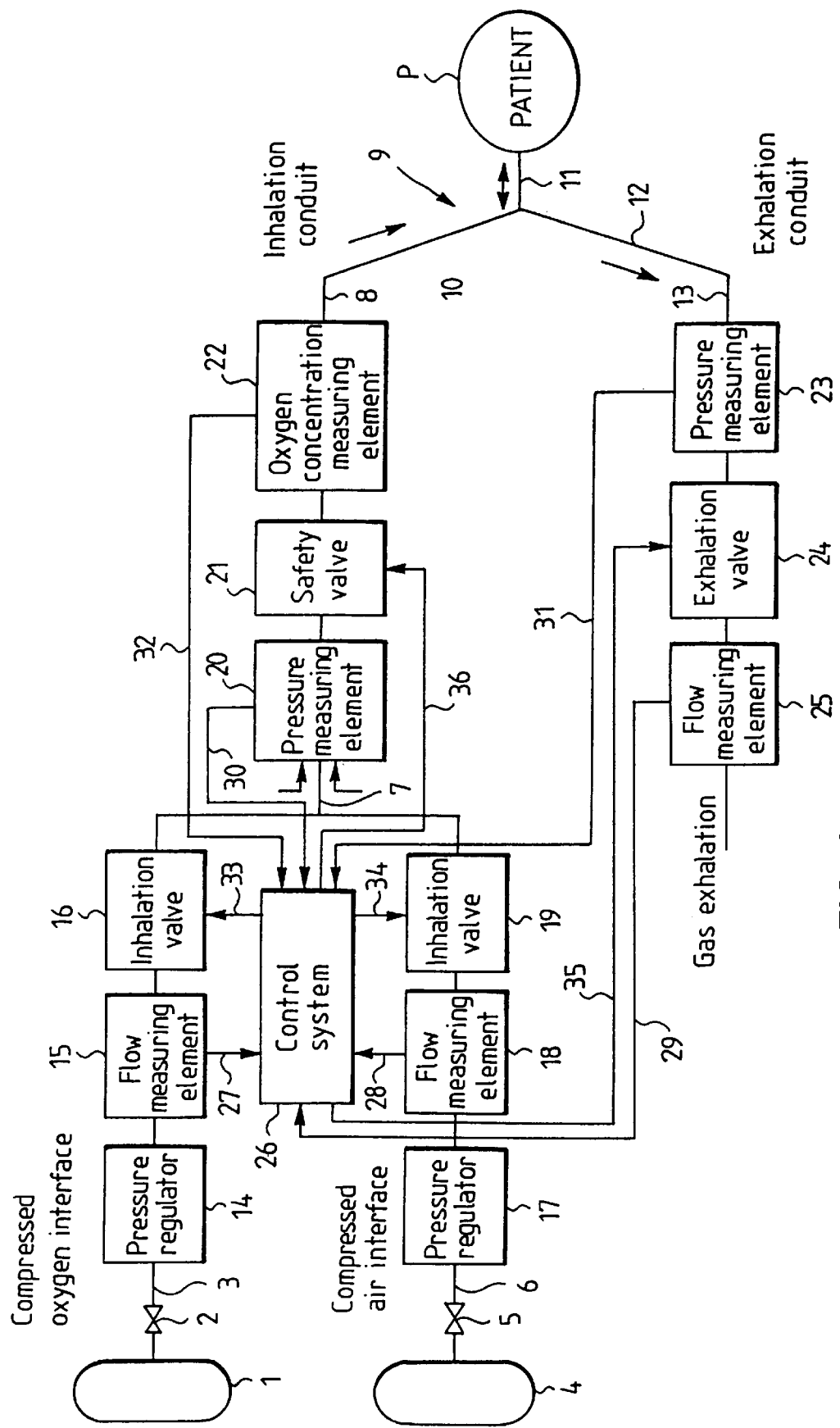
FIG. 1 illustrates an operational block diagram of a ventilator of the invention used in intensive care and the connection of a patient thereto.

A ventilator shown in FIG. 1 comprises a compressed oxygen interface 2, including a compressed oxygen conduit 3, to be connected to a compressed oxygen tank 1; a compressed air interface 5, including a compressed air conduit 6, to be connected to a compressed air tank 4; a gas mixture conduit 7, where the compressed oxygen and the compressed air conduits 3 and 6 are joined; an inhalation conduit 8 as an extension of a gas mixture conduit 7, said inhalation conduit being connected to a branch 10 of a Y piece 9, other branches of the Y piece 9 being a patient branch 11 and a branch 12 leading to an exhalation conduit 13 of the ventilator.

In conduit 3 are arranged a pressure regulator 14, a flow measuring element 15 and an inhalation valve 16 and, correspondingly, in conduit 6 a pressure regulator 17, a flow measuring element 18 and an inhalation valve 19.

The pressure regulators 14 and 17 are used for providing constant level of pressure in pressure tanks 1 and 4, which improves flow adjustability and reduces the requirements set for inhalation valves 16 and 19 used for controlling the flow in conduits 3 and 6.

In a gas mixture and inhalation conduit assembly 7, 8, in turn, are arranged a pressure measuring element 20, a safety valve 21, which will be later described in detail, and an oxygen concentration measuring element 22.

An exhalation conduit 13 is provided with a pressure measuring element 23, an exhalation valve 24 and a flow measuring element 25.

A patient P is connected to the branch 11 by a breathing mask or an intubation tube (not shown in the drawings), inhalation being performed by an over-pressured gas mixture delivered of pressure tanks 1 and 4 through the inhalation valves 16 and 19 to the inhalation conduit 8, whereby pressure in the inhalation conduit 8 rises. The exhalation conduit 13 is kept closed by the exhalation valve 24, so the gas mixture is conveyed further to the lungs of the patient P, causing also a rise in pressure there.

Exhalation takes place spontaneously by the releasing of the overpressure stored in the lungs during inhalation. This is achieved by the closing of the inhalation valves 16 and 19 and by the opening of the exhalation valve 24, whereby the impact of the pressure of the inhalation and exhalation conduits 8 and 13 acting on the patient P reduces. The over-pressure in the lungs then discharges in the form of a gas flow through the exhalation conduit 13.

The arrangement shown in FIG. 1 further comprises a control system 26, which receives information over paths 27, 28 and 29 from flow measuring elements 15, 18 and 25; over paths 30 and 31 from pressure measuring elements 20 and 23 and over a path 32 from an oxygen concentration measuring element 22. On the basis of the measurement data received, the system 26 controls, when necessary, the inhalation valves 16, 19 over the paths 33 and 34; the exhalation valve 24 over the path 35 and the safety valve 21 over the path 36.

It is also to be noted that in the above described system the location of the pressure measuring elements 20 and 23 is not essential and at least the flow measuring elements 15 and 18 can in some cases possibly be left out.

In principle, one pressure measuring element is sufficient, said element being arranged between the inhalation and exhalation valves, e.g. in the conduits 7, 8, 11, 12 or 13.

If, on the other hand, the ventilator in question is one in which pressure is created for instance with a blower, the construction of the ventilator can be considerably simpler. The above described system, at its simplest, then comprises one compressed gas interface (a blower which can be used for replacing the compressed air interface and the valve associated with it); the inhalation conduit 7, 8, arranged as an extension to said blower; the pressure measuring elements 20, an over-pressure restrictor valve, a valve allowing breathing from the atmosphere, a directional valve for inhalation, arranged in connection with the inhalation conduit; the exhalation conduit 13, including the exhalation valve 24 and a directional valve for exhalation; the Y piece 9; the control system 26; and the safety valve 21. With the exception of the safety valve 21 and the related control, which will be described later, this construction represents conventional technology, so it is not separately shown in the drawings and it will not be described here in any further detail.

The general operation of a system according to above described FIG. 1, correspondingly, has been already described in detail at the beginning in connection with the description of the prior art, with the exception of the safety valve 21 and the related control, so instead of going into this operation here in further detail, let us now concentrate on the description of the safety valve 21 essential to the invention and its structure and operation, particularly with reference to a structure shown in FIG. 1.

Figure 2:
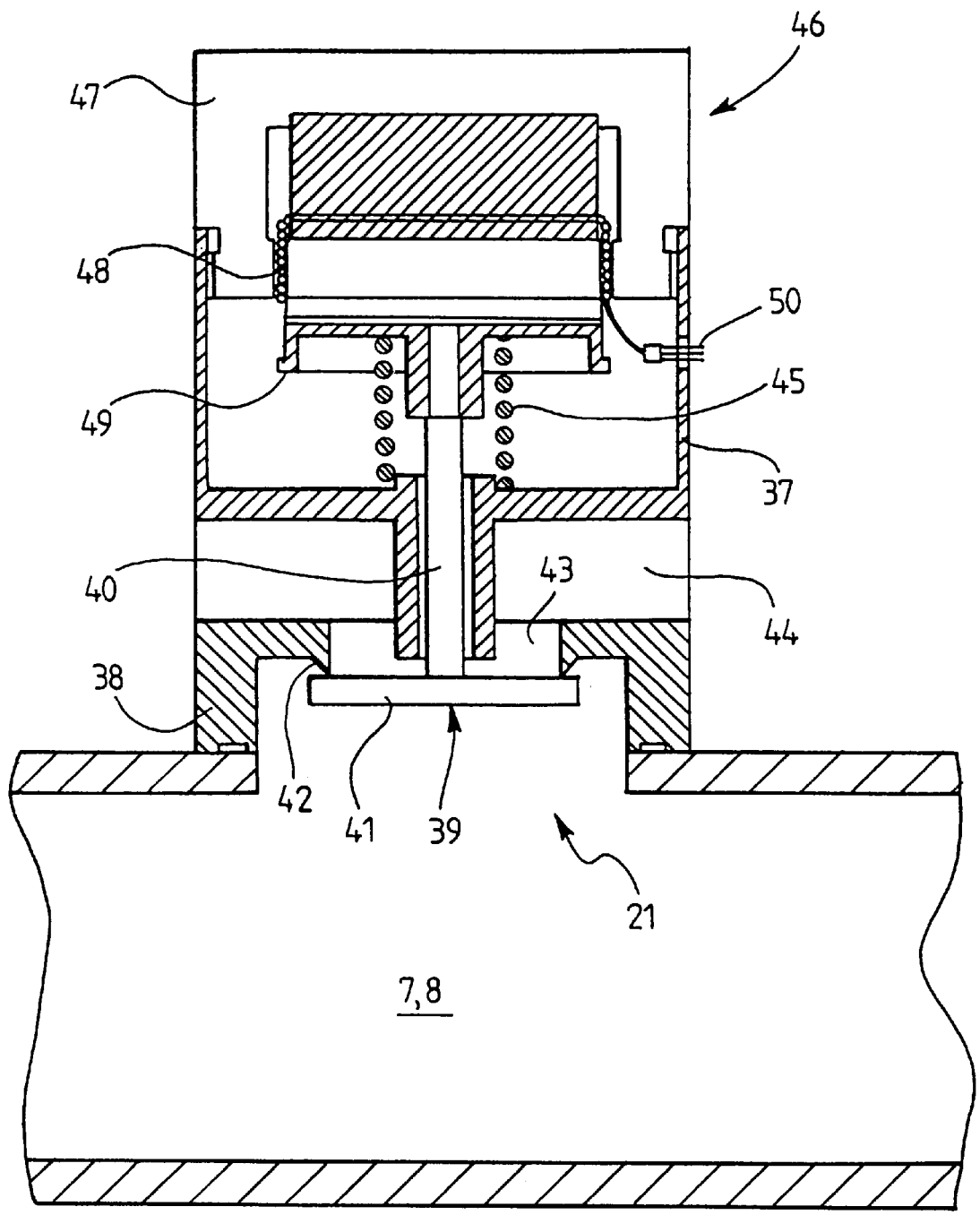
FIG. 2 illustrates a cross-section of a safety valve of the invention.

The safety valve 21 shown in the example illustrated by FIG. 2 comprises a vertical, elongated valve housing 37, the top part of which is provided with a ring-shaped part 38 which is used to attach the safety valve to the selected ventilator conduit. A closing element 39 is arranged in the housing 37 for a movement parallel to the axis of the housing 37. The closing element 39 comprises a rod 40 for enabling said movement and a valve plate 41 which, when the valve is in a closed position, seals against a seat 42 of a preferably triangular cross-sectional profile, arranged on the housing 37. Channels 43 and 44 are arranged in the housing 37 to allow connection from the selected ventilator conduit to the atmosphere when the valve is in an open position. It is to be noted here that the seat structure can naturally also consist of for instance a level surface and a sealing possibly associated with it.

The valve 21 is most advantageously arranged in the inspiration branch of the ventilator, in other words, in the gas mixture and inhalation conduit assembly 7, 8, for instance at the point shown in FIG. 1, in a substantially vertical position according to FIG. 2, wherein the closing element 39 normally seals against the seat 42 by a spring means 45 arranged between the housing 37 and the valve 21. This sealing becomes more effective by the over-pressure during inhalation.

To ensure that the valve 21 closes, a bidirectional actuator 46, comprising a permanent magnet 47 and a coil 48, is arranged between the housing 37 and the rod 40, said actuator forcing the valve plate 41 against the seat 42 by pulling the valve arrangement 40, 41, 49 upward when an electric current is supplied to the actuator 46 via leads 50. Since a primary closing force is provided by the spring 45 and by over-pressure during inhalation, the force the actuator 46 exercises on the closing element 39 can be small. The control system 26 can supply electrical current into the coil in both directions. This makes the magnet-coil system 47, 48 either pull or push the valve arrangement 40, 41, 49. An advantage of this single actuator system compared with double actuator systems is that in the case of any single malfunction the actuator does not need to act against another actuator force. Another advantage of the device is its smaller size and simpler mechanical construction.

Should the pressure during ventilation exceed the over-pressure limit set for the safety valve 21, the control system 26 activates the actuator 46 to act downward, wherein the closing element 39 disengages from its seat 42 to release the pressure in the inhalation conduit 8. The actuator 46 must be strong enough, because in a situation of malfunction the pressure in the inhalation conduit 8 can become even as high as the 12 kPa mentioned earlier and the closing surface of the closing element 39 is large, allowing thus low resistance to spontaneous breathing (described later). In a malfunction situation the second actuator has to work against the force of the spring 45.

Spontaneous breathing from the atmosphere through the safety valve 21 provided with the actuator 46 becomes possible when the actuator is released, which happens automatically for instance when the ventilator is not connected to power mains or it loses the electrical driving force for one reason or another. The under-pressure created by the patient's inhalation then causes under-pressure also in the inhalation and exhalation conduits 8 and 13. Said under-pressure causes the directional valve (not shown in the drawings) of the exhalation conduit 13 to close and the closing element 39 of the valve 21 of the invention to open against the force of the spring 45. Since the valve is located in the gas mixture and inhalation conduit assembly 7, 8, inhalation is performed over said assembly from the atmosphere through the channels 43 and 44 in the valve 21. The under-pressure that the valve 21 requires in order to open depends on the spring force of the spring 45. To minimise breathing effort, the force of the spring 45 must therefore be as small as possible. The over-pressure caused by exhalation in the inhalation branch 7, 8 and, on the other hand, the mass of the closing element 39 in turn cause the valve 21 and thus the whole inhalation conduit to close. Since the overpressure can be small, the force of the spring 45 must be sufficient for exceeding the friction forces acting on it. The same over-pressure also acts on the exhalation conduit 13 and on the directional valve therein by opening it. The two directional valves in the system, i.e. the actual safety valve 21 and the directional valve for exhalation, thus effectively prevent return breathing.

The safety valve 21 of the invention therefore constructionally provides an over-pressure restrictor valve and a valve enabling breathing from the atmosphere and, mainly operationally, a directional valve for inhalation, said valves being monitored and controlled by the above described control system 26, which receives its most important control data from the pressure measuring element 20.

The above description is only an example of the invention and only meant to illustrate the invention. A person skilled in art can, however, implement the details of the invention in various alternative ways.

What is claimed is:

1. A ventilator for intensified breathing, said ventilator comprising:

at least one compressed gas interface (2,3; 5,6) for inhalation gas;

an inhalation conduit (7,8) connected to the compressed gas interface (2,3; 5,6) for inhalation of said gas;

a pressure measuring element (20) for inhalation gas, said element being arranged in connection with the inhalation conduit (7,8);

a restrictor valve for releasing an over-pressure in the inhalation conduit;

a valve arranged in the inhalation conduit, said valve opening upon under-pressure in the inhalation conduit thereby allowing breathing from the atmosphere through the inhalation conduit;

a directional valve for inhalation, arranged in the inhalation conduit;

an exhalation conduit (13) for exhalation gas, including an exhalation valve (24) and a directional valve for exhalation; and a control system (26), which controls the over-pressure restrictor valve on the basis of the pressure measurement of the inhalation gas, whereby the over-pressure restrictor valve and the valve that makes breathing from the atmosphere possible are combined to provide a safety valve (21), which is arranged to be controlled by said control system (26) and which comprises;

a closing element (39);

means (46) for opening the closing element; and a connection (43,44) to the atmosphere, said connection to atmosphere being opened and closed by said closing element (39), characterized in that the closing element (39) is arranged in the safety valve (21) in such a way that the closing element remains in a closed position by the impact of a force other than gravity, and whereby said safety valve (21) also provides a directional valve for inhalation, which closes during exhalation the connection (43,44) to the atmosphere.

2. A ventilator according to claim 1, characterized in that it comprises only one compressed gas interface, which is provided by a blower.

3. A ventilator according to claim 1, characterized in that the pressure measuring element (20) is located between the inhalation and exhalation conduits.

4. A ventilator according to claim 1, characterized in that it comprises a compressed oxygen interface (2), including compressed oxygen conduits (3), provided with a pressure tank (1), a compressed air interface (5), including compressed air conduits (6), provided with a pressure tank (4), a gas mixture conduit (7) where the flows from compressed oxygen and compressed air conduits (3, 6) are combined.

5. A ventilator according to claim 4, characterized in that flow measuring elements (15, 18) and inhalation valves (16, 19) are arranged in compressed oxygen and compressed air conduits (3, 6), oxygen concentration measurement elements (22) are arranged in the gas mixture and inhalation conduit assembly (7, 8), pressure measuring elements (23) and flow measuring elements are arranged in the exhalation conduit (13), whereby the control system (26) also controls the inhalation valves and the exhalation valve on the basis of the measured pressures and flows.

6. A ventilator according to claim 1, characterized in that a spring means (45) is arranged for closing the closing element (39).

7. A ventilator according to claim 1, characterized in that it comprises an actuator (46) that can both close and open the closing element (39).

8. A safety valve connected to a patient conduit (7,8) of an apparatus for intensified breathing, said valve providing in the patient conduit (7,8) a restrictor valve for an over-pressure of the inhalation gas, and a valve allowing breathing from the atmosphere through the patient conduit, said safety valve being controllable by a control system (26) connected to it, said control system issuing control commands to the safety valve on the basis of the inhalation gas pressures measured in the patient conduit and said safety valve comprising a closing element (39), means (46) for opening the closing element and a connection (43,44) to the atmosphere, said closing element (39) enabling the connection to atmosphere to be selectively opened and closed, characterized in that the closing element (39) is arranged in the safety valve (21) in such a way that it remains in a closed position by the impact of a force other than gravity, whereby said safety valve (21) also provides a directional valve for inhalation, which closes the connection (43,44) to the atmosphere during exhalation.

9. A valve according to claim 8, characterized in that a spring means (45) is arranged for closing the closing element.

10. A valve according to claim 8, characterized in tat it comprises an actuator (46) which can both close and open the closing element (39).

11. A valve according to claim 9, characterized in that it comprises an actuator (46) which can both close and open the closing element (39).

12. A ventilator for intensified breathing, the ventilator comprising:

at least one compressed gas interface (2,3; 5,6) for inhalation gas;

an inhalation conduit (7,8) connected to the compressed gas interface for the inhalation of the gas;

a pressure measuring element (20) for the inhalation gas, the pressure measuring element being arranged in connection with the inhalation conduit;

a safety valve (21) connected to the inhalation conduit, the safety valve being operable to release an over-pressure of inhalation gas in the patient conduit and to allow breathing from the atmosphere through the patient conduit, the safety valve including a connection (43,44) to atmosphere, the connection to atmosphere being controlled by the opening and closing of a closing element (39), the closing element being arranged in the safety valve such that the closing element remains in a closed position by a force other than gravity such that the closing element closes the connection to atmosphere during exhalation and is movable against the force to an open position upon an under-pressure in the inhalation conduit during inhalation, the safety valve further including a means (46) for moving the closing element between the open and closed positions;

a control system (26) connected to the means for opening and closing the closing element, the control system issuing a command to the means for opening the closing element based upon an over-pressure measurement of the inhalation gas; and an exhalation conduit (13) for exhalation gas, including an exhalation valve (24) and a directional valve for exhalation.

13. The ventilator of claim 12, wherein the means for moving the closing element includes an actuator (46) operable to move the closing element between the open and closed positions.

14. The ventilator of claim 13, wherein the actuator includes a stationary permanent magnet (47) and a coil (48) mounted to the closing element, wherein energization of the coil moves the closing element between the open and closed positions.

* * * * *